(12) United States Patent
Seong et al.

(10) Patent No.: US 11,860,166 B2
(45) Date of Patent: Jan. 2, 2024

(54) RED FLUORESCENT PROTEIN-BASED BIOSENSOR FOR MEASURING ACTIVITY OF DOPAMINE RECEPTOR D1

(71) Applicant: KOREA INSTITUTE OF SCIENCE AND TECHNOLOGY, Seoul (KR)

(72) Inventors: Jihye Seong, Seoul (KR); Hyun-bin Kim, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 775 days.

(21) Appl. No.: 16/778,306

(22) Filed: Jan. 31, 2020

(65) Prior Publication Data

US 2021/0096133 A1 Apr. 1, 2021

(30) Foreign Application Priority Data

Sep. 30, 2019 (KR) .................. 10-2019-0120561

(51) Int. Cl.
| | |
|---|---|
| *G01N 33/58* | (2006.01) |
| *C07K 14/435* | (2006.01) |
| *C07K 14/705* | (2006.01) |
| *G01N 33/94* | (2006.01) |
| *C12N 15/85* | (2006.01) |
| *C12N 15/62* | (2006.01) |

(52) U.S. Cl.
CPC ..... *G01N 33/582* (2013.01); *C07K 14/43504* (2013.01); *C07K 14/70571* (2013.01); *C12N 15/62* (2013.01); *C12N 15/85* (2013.01); *G01N 33/9413* (2013.01); *C07K 2319/60* (2013.01)

(58) Field of Classification Search
CPC .......... C07K 14/70571; C07K 2319/60; C12N 15/62; C12N 15/85; G01N 33/9413
See application file for complete search history.

(56) References Cited

U.S. PATENT DOCUMENTS

2005/0287602 A1* 12/2005 O'Dowd ................ C07K 14/71
435/7.2

FOREIGN PATENT DOCUMENTS

KR 1020130085737 A 7/2013

OTHER PUBLICATIONS

Shi (PLOS One 2011 6:e20505). (Year: 2011).*
Rho (Biotechnology and Bioprocess Engineering 2013 18:1135-1141). (Year: 2013).*
Patriarchi T. et al., Ultrafast neuronal imaging of dopamine dynamics with designed genetically encoded sensors. Science. Jun. 29, 2018, vol. 360, eaat4422 (8 pages).

* cited by examiner

*Primary Examiner* — Changhwa J Cheu
(74) *Attorney, Agent, or Firm* — CANTOR COLBURN LLP (57) ABSTRACT

Provided are a red fluorescent protein-based biosensor for measuring the activity of dopamine receptor D1, a method of measuring the activity of dopamine receptor D1 using the biosensor, and a method of detecting a ligand binding to dopamine receptor D1.

14 Claims, 4 Drawing Sheets
(3 of 4 Drawing Sheet(s) Filed in Color)
Specification includes a Sequence Listing.

FIG. 6A
SEQ ID NO: 1. (amino acid sequence of dopamine receptor D1)

MRTLNTSAMDGTGLVVERDFSVRILTACFLSLLILSTLLGNTLVCAAVIRFRHLRSKVTNFFVISLAVSDLLVAVLVMPWKAVAEIAGFWP
FGSFCNIWVAFDIMCSTASILNLCVISVDRYWAISSPFRYERKMTPKAAFILISVAWTLSVLISFIPVQLSWHKAKPTSPSDGNATSLAETI
DNCDSSLSRTYAISSSVISFYIPVAIMIVTYTRIYRIAQKQIRRIAALERAAVHAKNCQTTTGNGKPVECSQPESSFKMSFKRETKVLKTLS
VIMGVFVCCWLPFFILNCILPFCGSGETQPFCIDSNTFDVFVWFGWANSSLNPIIYAFNADFRKAFSTLLGCYRLCPATNNAIETVSINN
NGAAMFSSHHEPRGSISKECNLVYLIPHAVGSSEDLKKEEAAGIARPLEKLSPALSVILDYDTDVSLEKIQPITQNGQHPT*

FIG. 6B
SEQ ID NO: 2. (amino acid sequence of modified red fluorescent protein)

LSSERVSERMYPEDGALKSEIKKGLRLKDGGHYAAEVKTTYKAKKPVQLPGAYIVDIKLDIVSHNEDYTIVEQCERAEGRHSTGGMDE
LYKGGTGGSLVSKGEEDNMAIIKEFMRFKVHMEGSVNGHEFEIEGEGEGRPYEAFQTAKLKVTKGGPLPFAWDILSPQFMYGSKAYI
KHPADIPDYFKLSFPEGFRWERVMNFEDGGIIHVNQDSSLQDGVFIYKVKLRGTNFPPDGPVMQKKTMGWEAYDDDL

FIG. 6C
SEQ ID NO: 3. (amino acid sequence of a signal peptide)

MKTIIALSYIFCLVFADYKDDDDAS

FIG. 6D
SEQ ID NO: 4. (amino acid sequence (indicated by blue) of dopamine receptor D1, the amino acid sequence (indicated by red) of the modified red fluorescent protein, and the amino acid sequence (indicated by yellow) of the signal peptide according to one specific embodiment)

MKTIIALSYIFCLVFADYKDDDDASIDMRTLNTSAMDGTGLVVERDFSVRILTACFLSLLILSTLLGNTLVCAAVIRFRHLRSKVTNFFVISL
AVSDLLVAVLVMPWKAVAEIAGFWPFGSFCNIWVAFDIMCSTASILNLCVISVDRYWAISSPARYERKMTPKAAFILISVAWTLSVLISFI
PVQLSWHKAKPTSPSDGNATSLAETIDNCDSSLSRTYAISSSVISFYIPVAIMIVTYTRIYRIAQKQLSSERVSERMYPEDGALKSEIKKG
LRLKDGGHYAAEVKTTYKAKKPVQLPGAYIVDIKLDIVSHNEDYTIVEQCERAEGRHSTGGMDELYKGGTGGSLVSKGEEDNMAIIKEF
MRFKVHMEGSVNGHEFEIEGEGEGRPYEAFQTAKLKVTKGGPLPFAWDILSPQFMYGSKAYIKHPADIPDYFKLSFPEGFRWERVMN
FEDGGIIHVNQDSSLQDGVFIYKVKLRGTNFPPDGPVMQKKTMGWEAYDDDLKRETKVLKTLSVIMGVFVCCWLPFFILNCILPFCGS
GETQPFCIDSNTFDVFVWFGWANSSLNPIIYAFNADFRKAFSTLLGCYRLCPATNNAIETVSINNGAAMFSSHHEPRGSISKECNLVY
LIPHAVGSSEDLKKEEAAGIARPLEKLSPALSVILDYDTDVSLEKIQPITQNGQHPT*

(Yellow): signal peptide
(Blue): DRD1 sequence
(Red): cpRFP module

FIG. 6E
SEQ ID NO: 5. (cDNA sequence of receptor dopamine D1)

ATGGACCCTCTGAATCTGTCATGGTATGACGATGATCTGGAAAGGCAAAACTGGTCCCGGCCGTTTAATGGATCAGATGGTAAA
GCAGATCGGCCTCACTACAATTACTACGCCACACTGCTCACCCTCCTCATTGCAGTTATTGTGTTCGGGAACGTGCTGGTTTGC
ATGGCAGTAAGCCGGGAAAAGGCTCTCCAGACAACTACCAACTACCTCATCGTCTCACTTGCGGTAGCAGACTTGCTGGTGGCT
ACCCTGGTCATGCCTTGGGTGGTTTACTTGGAGGTTGTTGGCGAGTGGAAGTTCTCAAGGATACATTGCGATATCTTTGTAACC
CTGGATGTTATGATGTGTACGGCTTCAATATTGAACCTCTGTGCCATCTCCATCGACCGCTATACTGCCGTAGCAATGCCTATGC
TTTACAATACCCGATATTCAAGCAAGCGGAGGGTGACGGTTATGATTTCCATCGTTTGGGTGCTGTCCTTTACGATTAGTTGCCC
TCTGCTGTTCGGGCTGAACAACGCAGACCAAAATGAGTGTATTATTGCCAATCCCGCCTTTGTGGTGTATTCATCAATTGTGAGC
TTTTACGTCCCATTTATTGTTACATTGTTGGTGTACATTAAAATATACATTGTCCTCAGGCGGCGGAGAAAACGGGTGAACACCA
AGCGGTCATCTAGAGCTTTCCGCGCTCATCTGAGAGCTCCACTGAAGGGCAACTGTACCCACCCGGAAGACATGAAACTGTGT
ACCGTCATCATGAAATCCAATGGGAGCTTCCCCGTTAATAGGCGGAGAGTGGAAGCCGCAAGGCGCGCACAGGAGCTGGAGA
TGGAGATGCTCAGCAGCACCAGCCCCCTGAGCGCACCCGGTACAGCCCCATTCCGCCCTCACATCACCAACTCACACTGCCC
GACCCCTCACATCATGGACTCCACTCTACCCCGGACTCACCGGCCAAGCCTGAAAAGAACGGGCACGCGAAAGATCACCCGAA
AATCGCTAAGATTTTCGAGATCCAAACTATGCCTAACGGCAAAACTCGCACCTCTCTGAAAACAATGAGTCGGAGAAAACTTTCA
CAGCAAAAGGAGAAGAAGGCCACCCAAATGCTGGCCATTGTACTCGGGGTGTTCATCATTTGTTGGCTGCCCTTTTTTATCACC
CACATCCTGAACATTCATTGTGATTGCAACATTCCACCAGTGCTCTATAGCGCCTTTACTTGGCTGGGTTATGTGAATAGTGCGG
TAAACCCCATAATCTACACCACATTCAATATCGAATTTCGAAAAGCATTTCTGAAGATTCTCCACTGT

FIG. 6F
SEQ ID NO: 6. (cDNA sequence of cpRFP )

CTGAGCTCACCCGTGGTTTCCGAGCGGATGTACCCCGAGGACGGCGCCCTGAAGAGCGAGATCAAGAAGGGGCTGAGGCTGA
AGGACGGCGGCCACTACGCCGCCGAGGTCAAGACCACCTACAAGGCCAAGAAGCCCGTGCAGCTGCCCGGCGCCTACATCGT
GGACATCAAGTTGGACATCGTGTGTCCCACAACGAGGACTACACCATCGTGGAACAGTGCGAACGCGCCGAGGGCGCCACTCC
ACCGGCGGCATGGACGAGCTGTACAAGGGGAGGTACAGCGGGAGTCTGGTGAGCAAGGGCGAGGAGGATAACATGGCCATC
ATCAAGGAGTTCATGCGCCTTCAAGGTGCACATGGAGGGCTCCGTGAACGGCCACGAGTTCGAGATCGAGGGCGAGGGCGAGG
GCCGCCCCTACGAGGCCTTTCAGACCGCTAAGCTGAAGGTGACCAAGGGTGGCCCCCTGCCCTTCGCCTGGGACATCCTGTC
CCCTCAGTTCATGTACGGCTCCAAGGCCTACATTAAGCACCCAGCCGACATCCCCGACTACTTCAAGCTGTCCTTCCCCGAGGG
CTTCAGGTGGGAGCGCGTGATGAACTTCGAGGACGGCGGCATTATTCACGTGAACCAGGACTCCTCCCTGCAGGACGGCGTAT
TCATCTACAAGGTGAAGCTGCGCGGCACCAACTTCCCCCCCGACGGCCCCGTAATGCAGAAGAAGACCATGGGCTGGGAGGC
TACGCGTGACGACCTG

RED FLUORESCENT PROTEIN-BASED BIOSENSOR FOR MEASURING ACTIVITY OF DOPAMINE RECEPTOR D1

CROSS-REFERENCE TO RELATED APPLICATION

This application claims the benefit of Korean Patent Application No. 10-2019-0120561, filed on Sep. 30, 2019, in the Korean Intellectual Property Office, the disclosure of which is incorporated herein in its entirety by reference.

SEQUENCE LISTING

This application includes a sequence listing submitted as an ASCII text file created Jan. 30, 2020, named 8H39247.TXT and having a file size of 14.8 Kb; the sequence listing is incorporated by reference herein.

BACKGROUND

1. Field

The present disclosure relates to a red fluorescent protein-based biosensor for measuring the activity of a dopamine receptor, and more specifically, a red fluorescent protein-based biosensor capable of selectively and sensitively measuring the activity of dopamine receptor D1, a method of measuring the activity of a dopamine receptor D1 using the biosensor, and a method of detecting a ligand binding to dopamine receptor D1.

2. Description of Related Art

Dopamine plays a very important role in the central nervous system, endocrine system, and cardiovascular system. Dopamine is, the most well-known catecholamine, one of the neurotransmitters that modulates signaling in the nervous system in vivo. A lack of dopamine in neurons causes serious diseases such as Parkinson's disease, schizophrenia, etc.

Dopamine is a neurotransmitter that is secreted to transmit certain signals between cranial nerve cells, and activates five known dopamine receptors (D1, D2, D3, D4, and D5) and variants thereof. Abnormalities in dopamine concentration and transmission cause many neurological diseases. Therefore, there is a need to develop a device for or a method of sensitively measuring the activity of dopamine receptors. In addition, depending on the subtypes or variants of the dopamine receptors, the mechanism of action in the body differs, and therefore, it is necessary to develop a device or a method capable of selectively measuring the dopamine receptor subtypes.

Patent document 1 describes a chemical sensor for detecting dopamine, in which a conductive polymer is coated with gold nanoparticles. As described, existing sensors exhibit high sensitivity, but have poor selectivity for dopamine receptor subtypes. In particular, it is difficult to measure biological analytes.

SUMMARY

An aspect provides a red fluorescent protein-based biosensor for measuring the activity of dopamine receptor D1.

Another aspect provides a method of measuring the activity of dopamine receptor D1.

Still another aspect provides a method of detecting a ligand binding to dopamine receptor D1.

Additional aspects will be set forth in part in the description which follows and, in part, will be apparent from the description, or may be learned by practice of the presented embodiments of the disclosure.

An aspect provides a red fluorescent protein-based biosensor for measuring the activity of dopamine receptor D1, the red fluorescent protein-based biosensor including:

a recombinant gene including a dopamine receptor D1 gene, and a gene encoding a red fluorescent protein or a modified red fluorescent protein;

a recombinant expression vector including the recombinant gene; or a transformant transformed with the recombinant expression vector.

Another aspect provides a method of measuring the activity of dopamine receptor D1 using the biosensor, the method including:

introducing the biosensor into cells;

adding a test sample to the biosensor-introduced cells; and measuring the activity of dopamine receptor D1 according to the addition of the test sample to the biosensor.

Still another aspect provides a method of detecting a ligand binding to dopamine receptor D1 using the biosensor, the method including: introducing the biosensor into cells;

adding a test sample to the biosensor-introduced cells; and detecting the ligand binding to dopamine receptor D1 according to the addition of the test sample to the biosensor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features, and advantages of certain embodiments of the disclosure will be more apparent from the following description taken in conjunction with the accompanying drawings, in which:

FIGS. 6A to 6F show amino acid sequences used in the preparation of the red fluorescent protein-based biosensor for measuring the activity of dopamine receptor D1 according to one specific embodiment; FIG. 6A shows an amino acid sequence (SEQ ID NO: 1) of dopamine receptor D1, FIG. 6B shows an amino acid sequence (SEQ ID NO: 2) of modified red fluorescent protein according to one specific embodiment; FIG. 6C shows an amino acid sequence (SEQ ID NO: 3) of a signal peptide according to one specific embodiment; FIG. 6D shows a recombinant amino acid sequence (SEQ ID NO: 4) including the amino acid sequence (indicated by blue) of dopamine receptor D1, the amino acid sequence (indicated by red) of the modified red fluorescent protein, and the amino acid sequence (indicated by yellow) of the signal peptide according to one specific embodiment; FIG. 6E shows a cDNA sequence (SEQ ID NO: 5) of receptor dopamine D1 according to one specific embodiment; and FIG. 6F shows a cDNA sequence (SEQ ID NO: 6) of cpRFP according to one specific embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Unless defined otherwise, all technical terms used herein have the same meanings as those generally understood by one of ordinary skill in the art to which the present disclosure belongs. Further, although methods or samples are described herein, those similar or equivalent thereto are also incorporated in the scope of the present disclosure. Processes described below are only one example according to the present disclosure. In the present disclosure, part of each process may be omitted or repeatedly performed, and in some cases, the order of the processes may be appropriately changed. The numerical values described herein are considered to include the meaning of "about", unless otherwise specified. The contents of all the publications disclosed as references herein are incorporated in the present disclosure.

An aspect provides a red fluorescent protein-based biosensor for measuring the activity of dopamine receptor D1, the red fluorescent protein-based biosensor including:

a recombinant gene including a dopamine receptor D1 gene, and a gene encoding a red fluorescent protein or a modified red fluorescent protein;

a recombinant expression vector including the recombinant gene; or a transformant transformed with the recombinant expression vector.

Figure 1A:
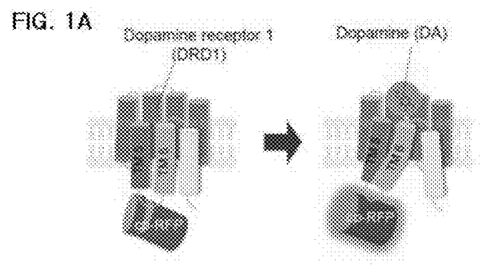
FIG. 1A is a schematic diagram illustrating a working principle and a mechanism of a red fluorescent biosensor for measuring the activity of dopamine receptor D1 (DRD1) and detecting a ligand (e.g., dopamine, DA) binding to DRD1.

FIG. 1A is a schematic diagram illustrating a working principle and a mechanism of a red fluorescent biosensor for measuring the activity of dopamine receptor D1 (DRD1) and detecting a ligand (e.g., dopamine, DA) binding to DRD1.

As used herein, "dopamine (DA or 3,4-dihydroxyphenethylamine, $C_8H_{11}NO_2$)", a catecholamine-based organic compound, refers to a hormone or neurotransmitter found in the central nervous system of various animals. Dopamine is one of the neurotransmitters secreted to transmit certain signals between cranial nerve cells, and activates dopamine receptors.

As used herein, the "dopamine receptor" is a type of G-protein coupled receptor (GPCR), and five subtypes (D1, D2, D3, D4, and D5 types) are known. The subtypes of the dopamine receptors may be further classified into D1-like receptors (D1 and D5) and D2-like receptors (D2, D3, and D4). The receptors are each unique in terms of intimacy with dopamine, binding to G proteins, signaling methods, distribution of specific neurons, etc. For example, D1-like receptors transduce signals to the cAMP pathway through separation of Gαs in the G protein, whereas D2-like receptors inhibit adenylate cyclase (AC) activity through separation of Gαi, resulting in reduction of cAMP levels.

In one specific embodiment, the dopamine receptor may be dopamine receptor D1. In another specific embodiment, the dopamine receptor D1 gene may encode an amino acid represented by SEQ ID NO: 1 (FIG. 6A).

As used herein, the "fluorescent protein" refers to a protein that exhibits fluorescence when exposed to light. Examples of the fluorescent protein may include a red fluorescent protein (RFP), a blue fluorescent protein (BFP), an enhanced blue fluorescent protein (EBFP), a cyan fluorescent protein (CFP), an enhanced cyan fluorescent protein (ECFP), a yellow fluorescent protein (YFP), an enhanced yellow fluorescent protein (EYFP), a green fluorescent protein (GFP), a modified green fluorescent protein, an enhanced green fluorescent protein (EGFP), etc.

In one specific embodiment, the fluorescent protein may be a red fluorescent protein or a modified red fluorescent protein. In one specific embodiment, the red fluorescent protein may be circularly permuted red fluorescent protein (cpRFP).

As used herein, the term "circular permutation" means a modification whereby new N- and C-termini are created in a protein (i.e., the protein is split into two parts), and original N- and C-termini of the protein are linked through an appropriate linker sequence.

In one specific embodiment, the circular permutation modification is induced in the fluorescent protein to change wavelength characteristics (e.g., absorption wavelength and/or fluorescence wavelength). In the circularly permuted fluorescent protein according to one specific embodiment, new N- and C-termini are located in close proximity to a chromophore which is necessary for fluorescence, and arbitrary proteins x and y are linked thereto such that fluorescence intensity is changed in response to their interaction. Based on this, a biosensor was developed.

Figure 1B:
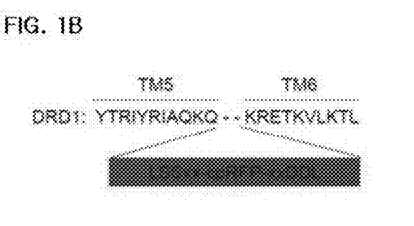
FIG. 1B is a schematic diagram illustrating modification of red fluorescent protein according to the kind and position change of a linker peptide (linker amino acids) introduced to optimize the biosensor for measuring the activity of dopamine receptor D1, wherein LSSxx represents a linker peptide composed of amino acids of leucine(L)-serine(S)-serine(S) linked to the N-terminus of cpRFP(cp-mApple) and any two amino acids (x)(x) linked thereto, and xxDDL represents a linker peptide composed of amino acids of aspartic acid (D)-aspartic acid (D)-leucine(L) linked to the C-terminus of cpRFP and any two amino acids (x)(x) linked thereto.

FIG. 1B is a schematic diagram illustrating modification of red fluorescent protein according to the kind and position change of a linker peptide (linker amino acids) introduced to optimize the biosensor for measuring the activity of dopamine receptor D1. LSSxx represents a linker peptide composed of amino acids of leucine(L)-serine(S)-serine(S) linked to the N-terminus of cpRFP and any two amino acids (x)(x) linked thereto. xxDDL represents a linker peptide composed of amino acids of aspartic acid (D)-aspartic acid (D)-leucine(L) linked to the C-terminus of cpRFP and any two amino acids (x)(x) linked thereto.

In one specific embodiment, the gene encoding the modified red fluorescent protein may include a gene encoding an amino acid sequence according to the following Formula 1:

$$L_1\text{-cpRFP-}L_2 \quad \text{[Formula 1]}$$

in Formula 1, $L_1$ includes a linker peptide having LSS and 1 to 5 amino acid residues at the N-terminus of cpRFP, and $L_2$ includes a linker peptide having 1 to 5 amino acid residues and DDL at the C-terminus of cpRFP. The amino acid residues may be any amino acid residues each independently selected. The amino acid residue may be selected from naturally occurring amino acids.

In one specific embodiment, in Formula 1, $L_1$ includes a linker peptide having LSS and any 2 independently selected amino acid residues at the N-terminus of cpRFP, and $L_2$ includes a linker peptide having any 2 independently selected amino acid residues and DDL at the C-terminus of cpRFP.

In one specific embodiment, $L_1$ includes $LSSX_1X_2$, and $L_2$ includes $X_3X_4DDL$, wherein $X_1$, $X_2$, $X_3$, and $X_4$ may be each independently any amino acid. For example, $X_1$, $X_2$, $X_3$, and $X_4$ may be each independently any one amino acid selected from the group consisting of alanine (A), cysteine (C), aspartic acid (D), glutamic acid (E), phenylalanine (F), glycine (G), histidine (H), isoleucine (I), lysine (K), leucine (L), methionine (M), asparagine (N), pyrrolysine (O), proline (P), glutamine (Q), arginine (R), serine (S), threonine (T), selenocysteine (U), valine (V), tryptophan (W), and tyrosine (Y).

In one specific embodiment, $X_1X_2$ may be any one selected from the group consisting of glutamic acid-arginine (ER), glutamine-arginine (QR), and arginine-arginine (RR), and $X_3X_4$ may be any one selected from the group consisting of tyrosine-aspartic acid (YD), threonine-serine (TS), and histidine-proline (HP).

In one specific embodiment, $X_1X_2$ may be glutamic acid-arginine (ER), and $X_3X_4$ may be tyrosine-aspartic acid (YD). The biosensor according to one specific embodiment may include a sequence of "LSS-ER-cpRFP-YD-DDL".

The receptor D1 biosensor including cpRFP having the substituted sequence exhibits high fluorescence intensity by reacting with a ligand binding to dopamine receptor D1, and has the excellent effect of measuring the activity of dopamine receptor D1.

In one specific embodiment, the gene encoding the modified red fluorescent protein may include a gene encoding an amino acid sequence represented by SEQ ID NO: 2 (FIG. 6(B)).

It is known that when G protein binding receptor (GPCR) is activated by ligands, its structural changes are most frequently found in Intracellular loop 3 (ICL3). In one specific embodiment, the amino acid sequence of the red fluorescent protein or the modified red fluorescent protein may bind to ICL3 of the dopamine receptor D1.

In one specific embodiment, the amino acid sequence of the red fluorescent protein or the modified red fluorescent protein may bind immediately after any one of the $1^{st}$ to $54^{th}$ amino acids from the N-terminus of ICL3 of dopamine receptor D1.

In one specific embodiment, the amino acid sequence of the red fluorescent protein or the modified red fluorescent protein may bind immediately after the $9^{th}$ amino acid from the N-terminus of ICL3 of dopamine receptor D1.

In one specific embodiment, the gene of the dopamine receptor D1 may encode a sequence in which any one amino acid of $120^{th}$ to $140^{th}$ amino acids of the amino acid sequence represented by SEQ ID NO: 1 is substituted with another amino acid.

In one specific embodiment, the gene of the dopamine receptor D1 may encode an amino acid sequence in which phenylalanine (F) at the $129^{th}$ position of the amino acid sequence represented by SEQ ID NO: 1 is substituted with alanine (A).

The receptor D1 biosensor including the amino acid sequence in which the amino acid at the 129$^{th}$ position in SEQ ID NO: 1 is substituted with alanine (A) exhibits high fluorescence intensity by reacting with the ligand binding to dopamine receptor D1, and has the excellent effect of measuring the activity of dopamine receptor D1.

The fluorescent biosensor for measuring the activity of dopamine receptor D1 according to one specific embodiment may measure the activity of dopamine receptor ligand at concentration of 0.05 μM, 0.1 μM, 0.5 μM, 1 μM, 1.5 μM, 5 μM, 6.25 μM, 10 μM, 12.5 μM, 50 μM, or 100 μM. The fluorescent biosensor for measuring the activity of dopamine receptor D1 according to one specific embodiment may effectively detect the dopamine receptor ligand at a concentration of 10 μM or more.

In one specific embodiment, the recombinant gene may further include a gene encoding a signal peptide. In one specific embodiment, the signal peptide may include an amino acid sequence represented by SEQ ID NO: 3 (FIG. 6C).

In one specific embodiment, the recombinant gene may include an amino acid sequence represented by SEQ ID NO: 4 (FIG. 6D).

Figure 2:
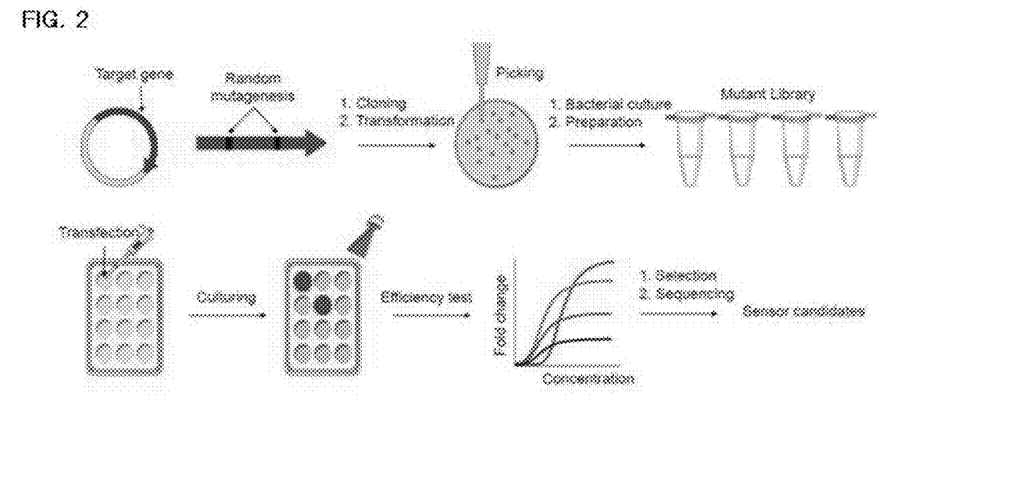
FIG. 2 is a schematic diagram illustrating a procedure of constructing candidate plasmids for preparing the biosensor for measuring the activity of dopamine receptor D1.

FIG. 2 is a schematic diagram illustrating a procedure of constructing candidate plasmids for preparing the biosensor for measuring the activity of dopamine receptor D1. To insert the nucleotide sequence of cpRFP into ICL3 of the dopamine receptor D1, based on cpRFP, any two independent linker amino acids were added after LSS linked to the N-terminus of cpRFP and before DDL linked to C-terminus of cpRFP. Random mutations were induced in two amino acids each immediately before and after cpRFP to construct candidate plasmids for the dopamine receptor D1 biosensor (FIG. 2).

Another aspect provides a method of measuring the activity of dopamine receptor D1 using the red fluorescent protein-based biosensor, the method including:
introducing the biosensor into cells;
adding a test sample to the biosensor-introduced cells; and
measuring the activity of the dopamine receptor D1 according to the addition of the test sample to the biosensor.

Still another aspect provides a method of detecting a ligand binding to the dopamine receptor D1 using the red fluorescent protein-based biosensor, the method including:
introducing the biosensor into cells;
adding a test sample to the biosensor-introduced cells; and
detecting the ligand binding to the dopamine receptor D1 according to the addition of the test sample to the biosensor.

In one specific embodiment, provided is a method of detecting dopamine or dopamine agonists using the red fluorescent protein-based biosensor.

As used herein, the term "gene" refers to any nucleotide sequence or part thereof that has a functional role in protein coding or transcription or regulation of other gene expression. The gene may consist of the entire of nucleotides encoding a functional protein or only a part of nucleotides encoding or expressing a protein. The nucleotide sequence may include exons, introns, initiation or termination regions, promoter sequences, other regulatory sequences, or gene abnormalities within a unique sequence adjacent to the gene.

As used herein, the "protein" also includes fragments, analogs, and derivatives thereof that retain biological activity or function substantially identical to that of a reference protein.

As used herein, the "transfection" refers to a process whereby extracellular DNA enters a host cell in the presence or absence of an accompanying substance. Transfected cells refer to cells having extracellular DNA by introducing the extracellular DNA to the cells. DNA may be introduced into cells so that it may be inserted into chromosome or it may replicate as an extrachromosomal material.

As used herein, the "transduction" is a phenomenon in which DNA of a bacterium is transferred to another bacterium via a virus. Transduction, even when a foreign DNA is introduced into another cell via a viral vector, is often used by molecular biologists to introduce a foreign gene into the host cell's genome.

As used herein, the "transformation" refers to a molecular biological phenomenon in which a DNA chain fragment or plasmid containing a gene of a different kind from that of original cells penetrate the cells and binds to DNA present in the original cells, and as a result, genetic characteristics of the cell are changed. Cells introduced with a foreign DNA, etc. are called 'transformant'.

As used herein, the term "vector" refers to any nucleic acid including a competent nucleotide sequence that is inserted into a host cell to be incorporated into the genome of the host cell by recombination, or to autonomously replicate as an episome. Such a vector may include a linear nucleic acid, a plasmid, a phagemid, a cosmid, an RNA vector, a viral vector, etc.

As used herein, the expression "about" or "approximately" means that a mentioned value may vary to some degree. For example, the value may vary to 10%, 5%, 2%, or 1%.

As used herein, the term "have", "may have", "include", or "may include" indicates existence of corresponding features (e.g., elements such as numeric values or components) but do not exclude presence of additional features. As used herein, the term "including" does not limit the present disclosure to exclude any modification or addition. Although described using the term "including", the method, substance, and composition described herein may be described using "consisting substantially of" or "consisting of". As used herein, the singular forms include plural forms unless the context clearly dictates otherwise.

EXAMPLES

Hereinafter, the present disclosure will be described in more detail with reference to the following Examples. However, the following Examples are only for illustrating the present disclosure, and the scope of the present disclosure is not limited by these Examples. As used herein, the term "to" includes the endpoint of the range and all midpoints therebetween. Those skilled in the art will understand that the numerical amount of deviation is possible. Therefore, it is understood that whenever a numerical value is mentioned in the specification or claims, the numerical value or any additional value relating to such a numerical value is also within the scope of the present disclosure.

Example 1. Preparation of Red Fluorescent Protein-Based Biosensor for Measuring Activity of Dopamine Receptor D1

(1) Construction of Genetic Recombinant Plasmid cDNA of human dopamine receptor D1 amplified by PCR was obtained (SEQ ID NO: 5). The gene of human dopamine receptor D1 encodes an amino acid represented by SEQ ID NO: 1. The amplified cDNA of dopamine receptor D1 thus obtained was fused into a pcDNA5/FRT plasmid vector digested with Cla1/Xho1 restriction enzymes using an infusion technique.

Further, cDNA of cpRFP which is circularly permuted red fluorescent protein was amplified by PCR (cDNA of cpRFP, SEQ ID NO: 6).

To optimize the biosensor for measuring the activity of dopamine receptor D1, a genetic recombinant plasmid was prepared, in which the amplified cpRFP was inserted into a specific site of ICL3 (immediately after the 9$^{th}$ amino acid from the N-terminus of ICL3 which is an intracellular loop 3 of dopamine receptor D1 (FIG. 1B).

To insert the nucleotide sequence of cpRFP into ICL3 of the dopamine receptor D1, 5 linker peptides (linker amino acids) were added before and after cpRFP, respectively such that LSSPV-cpRFP-TDDDL was prepared.

(2) Random Mutagenesis and Transfection

In the recombinant amino acid sequence ($LSSX_aX_b$-cpRFP-$X_cX_d$DDL) including the linker peptides each linked to the N- and C-termini of cpRFP, random mutation was induced in two amino acids each immediately before and after cpRFP to prepare candidate plasmids for the dopamine receptor D1 biosensor (FIG. 2).

A variety of genetic recombinant dopamine receptor D1 plasmids were constructed using a principle of the cpRFP-based biosensor, in which the brightness of the sensor varies depending on the linker peptide arrangement. In the linker peptides ($LSSX_aX_b$ and $X_cX_d$DDL) each linked to the N- and C-termini of cpRFP, random mutation was induced in two amino acids ($X_aX_b$ and $X_cX_d$) each immediately before and after cpRFP to substitute $X_aX_b$ and $X_cX_d$ with glutamic acid-arginine(ER) and tyrosine-aspartic acid (YD), respectively.

(3) Selection of Candidate Plasmids for Dopamine Receptor D1 Biosensor and Cell Culture After transformation into *Escherichia coli* as a competent cell, a large amount of genetic recombinant plasmids were obtained through cloning. Subsequently, isolation and purification were performed, and then plasmids of the sensor for measuring the activity of dopamine receptor D1 were obtained through sequencing.

Each plasmid was transfected into an animal cell HEK293A, followed by cell culture. The HEK293A cell line was seeded on a cell culture dish at an equal density, and cultured at a temperature of 37° C. and 5% $CO_2$ for about 16 hours. Thereafter, 2 µl of Lipofectamine 2000 and the prepared dopamine receptor D1 biosensor (1 µg) were stabilized in an Opti-MEM medium (ThermoFisher Scientific) for 20 minutes, and then added to subcultured cells.

6 hours after transfection, cells were subcultured in a mini-confocal dish coated with fibronectin, and DMEM (Hyclone, SH30604.01) containing 10% (v/v) fetal bovine serum (FBS) (Hyclone, SH30084.03) and 0.5% penicillin/streptomycin (Corning, 30-002-CI) was added, followed by culturing overnight. Next day, observation was performed using a live fluorescence microscope. Through the live fluorescence microscope, HEK293A single cells transfected with the biosensor for measuring the activity of dopamine receptor D1 were observed.

To measure the activity of dopamine receptor D1, the dopamine receptor D1 biosensor is required to locate in the cell membrane of animal cell HEK293A. Thus, whether the biosensor located in the cell membrane of animal cell HEK293A was examined through a fluorescence microscope. Further, according to the principle of the cpRFP-based biosensor, in which the brightness of the sensor varies depending on the linker peptide arrangement, sensor candidates with high expression efficiency were imaged using the fluorescence microscope, after treatment of the medium with dopamine.

(4) Measurement of Activity of Dopamine Receptor D1 Using Dopamine Receptor D1 Biosensor The prepared dopamine receptor D1 biosensor was treated with a ligand of dopamine receptor D1 (agonist), and fluorescence intensity before and after the treatment was measured in real time to determine intensity change.

First, dopamine which is a ligand of dopamine receptor D1 was prepared at a final concentration of 10 µM and added to a system. To minimize a photobleaching phenomenon, the live fluorescence microscope was set. When stimulated with light at a wavelength of 560 nm in the live fluorescence microscope, intensity at a cpRFP fluorescence wavelength of 610 nm was measured.

To induce fluorescence intensity suitable for experiments, 50 msec exposure and ND16 intensity were maintained. The fluorescence cycle was performed for total 10 minutes by measuring cpRFP images for 1 minute using the fluorescence microscope.

The saved images were analyzed using an NIS program (Nikon). cpRFP fluorescence intensity of the entire single cells in the regions of interest (ROI) was analyzed in the NIS program. Change of the corresponding fluorescence intensity means efficiency of the biosensor for measuring the activity of dopamine receptor D1 in the single cell. After acquiring the change of fluorescence intensity over time, the fluorescence intensity before adding the ligand dopamine was averaged and set as Fo, and the change of fluorescence intensity over time was set as F, and then F/Fo data were made and normalized.

Figures 3A, 3B:
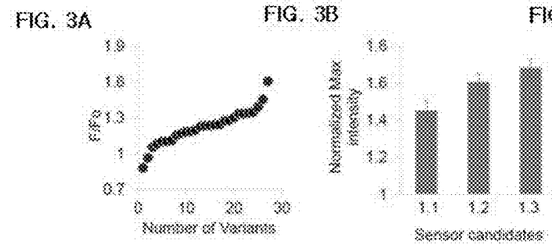
FIG. 3A is a graph showing changes (F/F$_0$) in fluorescence intensity of the biosensor candidates for measuring the activity of dopamine receptor D1 with respect to dopamine as an agonist, wherein the X-axis represents the number of the biosensor candidates (number of variants) tested, the fluorescence intensity of the biosensor candidate corresponding to each number was measured, and their effects on measuring the activity of dopamine receptor D1 were evaluated.
FIG. 3B is a graph showing results of measuring the degree of increase of the maximum fluorescence intensity (y axis: normalized maximum intensity) according to the addition of dopamine by using three candidates (DRD1 Red 1.1, 1.2, and 1.3) having excellent efficiency among the biosensor candidates for measuring the activity of dopamine receptor D1.

FIG. 3A is a graph showing changes ($F/F_0$) in fluorescence intensity of the biosensor candidates for measuring the activity of dopamine receptor D1 with respect to dopamine as an agonist. The X-axis represents the number of the biosensor candidates (number of variants) tested. The fluorescence intensity of the biosensor candidate corresponding to each number was measured, and their effects on measuring the activity of dopamine receptor D1 were evaluated. FIG. 3B is a graph showing results of measuring the degree of increase of the maximum fluorescence intensity (y axis: normalized maximum intensity) according to the addition of 10 µM dopamine by using three candidates (DRD1 Red 1.1, 1.2, and 1.3) having excellent efficiency among the biosensor candidates for measuring the activity of dopamine receptor D1.

Figure 3C:
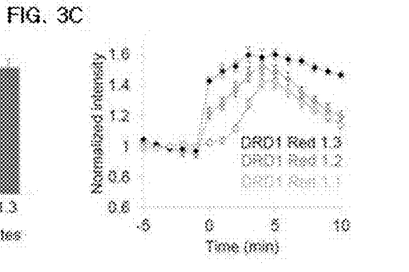
FIG. 3C is a graph showing results of measuring the change in the fluorescence intensity (y axis: normalized intensity) over time by using three candidates (DRD1 Red 1.1, 1.2, and 1.3) having excellent efficiency among the biosensor candidates for measuring the activity of dopamine receptor D1.

DRD1 Red 1.1 represents a prototype sensor prepared by cloning using the dopamine receptor D1 gene and the original red fluorescent protein. As shown in FIG. 2, DRD1 Red 1.2 and DRD1 Red 1.3 represent two candidates that exhibited high fluorescence intensity at the time of measuring the effects of the biosensors using the candidate plasmids for the dopamine receptor D1 biosensor which were prepared by inducing random mutation in two amino acids each immediately before and after cpRFP. DRD1 Red 1.2 and DRD1 Red 1.3 include, in common, "LSS-ER-cpRFP-YD-DDL" sequence, which was prepared by substituting two amino acids each immediately before and after cpRFP in the linker peptides ($LSSX_aX_b$ and $X_cX_d$DDL) linked to each of the N- and C-termini of cpRFP with glutamic acid-arginine (ER) and tyrosine-aspartic acid (YD), respectively. As shown in FIGS. 3B and 3C, DRD1 Red 1.2 and DRD1 Red 1.3 exhibited higher fluorescence intensity than DRD1 Red 1.1, indicating that they are excellent red fluorescent biosensors for measuring the activity of dopamine receptor D1.

DRD1 Red 1.3 includes a substitution of alanine (A) for phenylalanine (F) at position 129 of the amino acid sequence (SEQ ID NO: 1) of dopamine receptor D1 in DRD1 Red 1.2.

As shown in FIGS. 3B and 3C, DRD1 Red 1.3 exhibited the highest fluorescence intensity, indicating that it is the most effective red fluorescent biosensor for measuring the activity of dopamine receptor D1 in terms of measuring the activity of dopamine receptor D1.

FIG. 3C is a graph showing results of measuring the change in the fluorescence intensity (y axis: normalized intensity) over time by using three candidates (DRD1 Red 1.1, 1.2, and 1.3) having excellent efficiency among the biosensor candidates for measuring the activity of dopamine receptor D1.

As shown in FIG. 3C, the change of fluorescence intensity was measured in real time, and as a result, candidate exhibiting a larger change in the fluorescence intensity and a high reaction rate were selected by inducing mutation and testing a larger number of candidates.

Example 2. Characterization of Red Fluorescent Biosensor for Measuring Activity of Dopamine Receptor D1

The red fluorescent biosensor for dopamine receptor D1 prepared in Example 1 was transfected into HEK293A cell line as in Example 1, and expressed therein, and expression of the dopamine receptor D1 biosensor on the membrane of HEK293A was examined using the live fluorescence microscope.

Figure 4A:
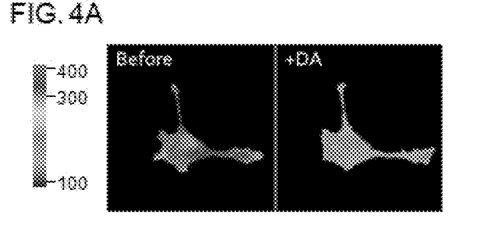
FIG. 4A shows images of a cell in which activation of a DRD1 Red 1.3 biosensor selected based on the results of FIG. 3 exhibited a color change when the biosensor was treated with dopamine at a concentration of 10 μM (left: before dopamine treatment, right: after dopamine treatment)

FIG. 4A shows images of a cell in which activation of the biosensor exhibited a color change when the biosensor was treated with dopamine which is a dopamine receptor D1 ligand at a concentration of 10 µM (left: before dopamine treatment, right: after dopamine treatment).

Figure 4B:
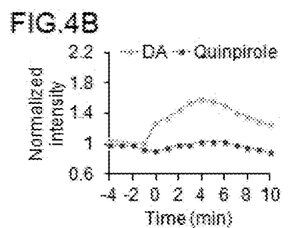
FIG. 4B is a graph showing results of measuring the increase in fluorescence intensity (y-axis: normalized intensity) over time when the fluorescent biosensor for measuring the activity of dopamine receptor D1 was treated with dopamine which is a dopamine receptor D1 ligand and quinpirole which is a dopamine receptor D2-selective ligand.

FIG. 4B is a graph showing results of measuring normalized intensity when the fluorescent biosensor for measuring the activity of dopamine receptor D1 was treated with dopamine which is a dopamine receptor D1 agonist and quinpirole which is a dopamine D2 receptor selective ligand. FIG. 4B shows that the dopamine receptor D1 fluorescent biosensor did not response to quinpirole which is a dopamine D2 receptor selective ligand.

Figure 4C:
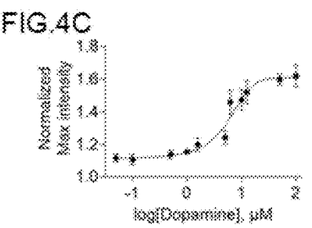
FIG. 4C is a graph showing maximum fluorescence intensity (y-axis: normalized maximum intensity) measured after adding, to the biosensor for measuring the activity of dopamine receptor D1, dopamine which is a dopamine receptor D1 ligand at a final concentration of 0.05 μM, 0.1 μM, 0.5 μM, 1 μM, 1.5 μM, 5 μM, 6.25 μM, 10 μM, 12.5 μM, 50 μM, or 100 μM in cell media.

FIG. 4C is a graph showing fluorescence intensity (y-axis: normalized intensity) of the biosensor for measuring the activity of dopamine receptor D1, measured after adding dopamine which is a dopamine receptor D1 ligand at a final concentration of 0.05 µM, 0.1 µM, 0.5 µM, 1 µM, 1.5 µM, 5 µM, 6.25 µM, 10 µM, 12.5 µM, 50 µM, or 100 µM in cell media. The intensity of the red channel that was specified by ROI through the NIS program (Nikon) performed in Example 1 was measured and analyzed.

As shown in FIG. 4C, the fluorescent biosensor for measuring the activity of dopamine receptor D1 according to one specific embodiment may detect activity for the dopamine receptor ligand at a concentration of 0.05 µM, 0.1 µM, 0.5 µM, 1 µM, 1.5 µM, 5 µM, 6.25 µM, 10 µM, 12.5 µM, 50 µM, or 100 µM. Further, the biosensor may effectively detect the dopamine receptor ligand at a concentration of 10 µM or more.

Figure 4D:
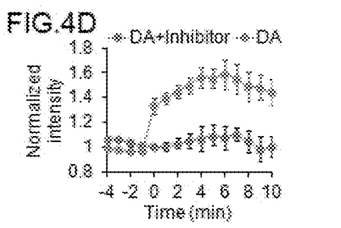
FIG. 4D is a graph showing fluorescence intensity (y-axis: normalized intensity) of the biosensor for measuring the activity of dopamine receptor D1 over time, when the fluorescent biosensor for measuring the activity of dopamine receptor D1 was co-treated with dopamine (DA) which is a dopamine receptor D1 ligand and a DA inhibitor (Haloperidol) (red plot) or treated with only dopamine (DA) (blue plot)

FIG. 4D is a graph showing fluorescence intensity (y-axis: normalized intensity) of the biosensor for measuring the activity of dopamine receptor D1 over time, when the fluorescent biosensor for measuring the activity of dopamine receptor D1 was co-treated with dopamine (DA) which is a dopamine receptor D1 ligand and an inhibitor (Haloperidol) (red plot) or treated with only dopamine (DA) (blue plot).

Figure 5A:
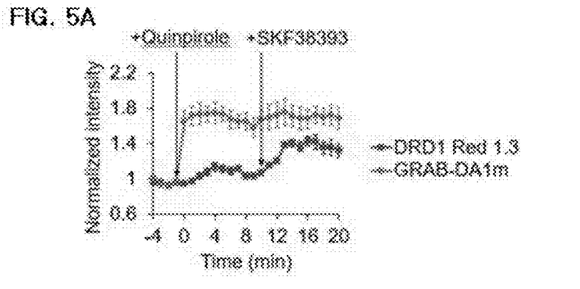
FIG. 5A shows results of performing co-fluorescent imaging using a green fluorescent biosensor (GRAB-DA1m) for measuring the activity of dopamine receptor D2 which was separately prepared for comparison with the red fluorescent biosensor for measuring the activity of dopamine receptor D1 (DRD1 Red 1.3), wherein the graph shows the increase in fluorescence by selective response of each fluorescent biosensor to each ligand, when first treated with quinpirole which is a D2-selective ligand, and then serially treated with SKF38393 which is a D1-selective ligand.

FIG. 5A shows results of performing co-fluorescent imaging using a green fluorescent biosensor (GRAB-DA1m) for measuring the activity of dopamine receptor D2 which was separately prepared for comparison with the red fluorescent biosensor for measuring activity of dopamine receptor D1 (DRD1 Red 1.3). The graph shows the increase in fluorescence by selective response of each fluorescent biosensor to each ligand, when first treated with quinpirole which is a D2 selective ligand, and then serially treated with SKF38393 which is a D1 selective ligand.

Figure 5B:
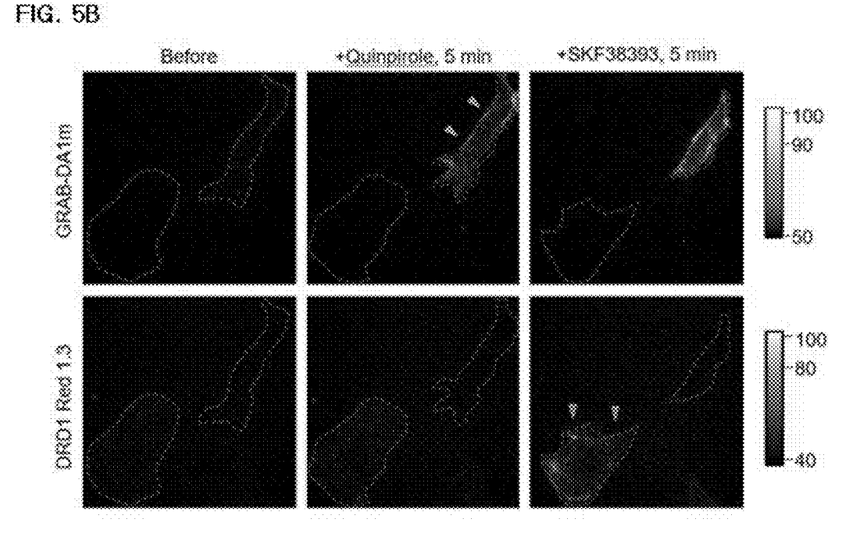
FIG. 5B shows results of performing fluorescent imaging before adding the ligand (Before), 5 minutes after treatment with quinpirole which a D2-selective ligand (+Quinpirole, 5 min), and 5 minutes after treatment with SKF38393 which is a D1-selective ligand (+SKF38393, 5 min) in the experiment explained in FIG. 5A; wherein the fluorescent images of cells each expressing the red fluorescent biosensor for measuring the activity of dopamine D1-type receptor (DRD1 Red 1.3) or the green fluorescent biosensor for measuring the activity of dopamine receptor D2 (GRAB-DA1m) are shown.

FIG. 5B shows results of performing fluorescent imaging before adding the ligand (Before), 5 minutes after treatment with quinpirole which a D2 selective ligand (+Quinpirole, 5 min), and 5 minutes after treatment with SKF38393 which is a D1 selective ligand (+SKF38393, 5 min) in the experiment explained in FIG. 5A. The fluorescent images of cells each expressing the red fluorescent biosensor for measuring the activity of dopamine receptor D1 (DRD1 Red 1.3) or the green fluorescent biosensor for measuring the activity of dopamine receptor D2 (GRAB-DA1m) are shown.

The red fluorescent protein-based biosensor according to an aspect may have selectivity depending on the dopamine receptor subtype, and may detect the activity of dopamine receptor D1 with high accuracy and resolution. Unlike the green fluorescent protein-based biosensor, the red fluorescent protein-based biosensor may detect the activity of dopamine receptor D1 with high accuracy without overlapping with excitation wavelength.

Further, when the red fluorescent protein-based biosensor and another fluorescent biosensor of different wavelength (e.g., green fluorescent protein biosensor) are used in combination, the dopamine activity may be measured by changes and interaction of two kinds of signals.

A method of measuring the activity of dopamine receptor D1 according to an aspect may sensitively measure activity of dopamine receptor D1 in live cells.

A method of detecting a ligand binding to dopamine receptor D1 according to another aspect may effectively and reversibly detect the ligand binding to dopamine receptor D1, e.g., dopamine or dopamine agonist.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A red fluorescent protein-based biosensor for measuring the activity of dopamine receptor D1, the biosensor comprising:
   a recombinant gene comprising a dopamine receptor D1 gene, and a gene encoding a modified circularly permuted red fluorescent protein (cpRFP) ;
   a recombinant expression vector comprising the recombinant gene; or
   a transformant transformed with the recombinant expression vector, wherein the gene encoding the modified circularly permuted red fluorescent protein (cpRFP) comprises a gene encoding an amino acid sequence of the following Formula 1:

$$L_1\text{-cpRFP-}L_2 \quad \text{[Formula 1]}$$

wherein, $L_1$ comprises a linker peptide having LSS and any 2 independently selected amino acid residues at the N-terminus of cpRFP, and $L_2$ comprises a linker peptide having any 2 independently selected amino acid residues and DDL at the C-terminus of cpRFP.

2. The biosensor of claim 1, wherein the dopamine receptor D1 gene encodes an amino acid sequence comprising SEQ ID NO: 1.

3. The biosensor of claim 1, wherein $L_1$ comprises $LSSX_1X_2$, and $L_2$ comprises $X_3X_4DDL$, wherein $X_1$, $X_2$, $X_3$, and $X_4$ are each independently any amino acid.

4. The biosensor of claim 3, wherein $X_1X_2$ is any one selected from the group consisting of glutamic acid-arginine (ER), glutamine-arginine (QR), and arginine-arginine (RR), and $X_3X_4$ is any one selected from the group consisting of tyrosine-aspartic acid (YD), threonine-serine (TS), and histidine-proline (HP).

5. The biosensor of claim 3, wherein $X_1X_2$ is glutamic acid-arginine (ER), and $X_3X_4$ is tyrosine-aspartic acid (YD).

6. The biosensor of claim 1, wherein the gene encoding the modified circularly permuted red fluorescent protein (cpRFP) comprises a gene encoding an amino acid sequence comprising SEQ ID NO: 2.

7. The biosensor of claim 1, wherein the amino acid sequence of the red fluorescent protein or the modified red fluorescent protein binds to Intracellular loop 3 (ICL3) of dopamine receptor D1.

8. The biosensor of claim 1, wherein the amino acid sequence of the modified circularly permuted red fluorescent protein (cpRFP) binds immediately after any one amino acid of the $1^{st}$ to $54^{th}$ amino acids from the N-terminus of Intracellular loop 3 (ICL3) of dopamine receptor D1.

9. The biosensor of claim 1, wherein the amino acid sequence the modified circularly permuted red fluorescent protein (cpRFP) binds immediately after the $9^{th}$ amino acid from the N-terminus of ICL3 of dopamine receptor D1.

10. The biosensor of claim 1, wherein the dopamine receptor D1 gene encodes an amino acid sequence in which phenylalanine (F) at the $129^{th}$ position of an amino acid sequence represented by SEQ ID NO: 1 is substituted with alanine (A).

11. The biosensor of claim 1, wherein the recombinant gene further comprises a gene encoding a signal peptide, wherein the signal peptide comprises an amino acid sequence comprising SEQ ID NO: 3.

12. The biosensor of claim 11, wherein the recombinant gene comprises an amino acid sequence comprising SEQ ID NO: 4.

13. A method of measuring the activity of dopamine receptor D1 using the biosensor of claim 1, the method comprising:
   introducing the biosensor of claim 1 into cells;
   adding a test sample to the biosensor-introduced cells; and
   measuring the activity of dopamine receptor D1 according to the addition of the test sample to the biosensor.

14. A method of detecting a ligand binding to dopamine receptor D1 using the biosensor of claim 1, the method comprising:
   introducing the biosensor of claim 1 into cells;
   adding a test sample to the biosensor-introduced cells; and
   detecting the ligand binding to dopamine receptor D1 according to the addition of the test sample to the biosensor.

* * * * *

SEQUENCE LISTING

<160> NUMBER OF SEQ ID NOS: 6

<210> SEQ ID NO 1
<211> LENGTH: 446
<212> TYPE: PRT

<213> ORGANISM: Artificial Sequence
<220> FEATURE:
<223> OTHER INFORMATION: The amino acid sequence of dopamine receptor D1 type

<400> SEQUENCE: 1

```
Met Arg Thr Leu Asn Thr Ser Ala Met Asp Gly Thr Gly Leu Val Val
1               5                   10                  15

Glu Arg Asp Phe Ser Val Arg Ile Leu Thr Ala Cys Phe Leu Ser Leu
            20                  25                  30

Leu Ile Leu Ser Thr Leu Leu Gly Asn Thr Leu Val Cys Ala Ala Val
        35                  40                  45

Ile Arg Phe Arg His Leu Arg Ser Lys Val Thr Asn Phe Phe Val Ile
    50                  55                  60

Ser Leu Ala Val Ser Asp Leu Leu Val Ala Val Leu Val Met Pro Trp
65                  70                  75                  80

Lys Ala Val Ala Glu Ile Ala Gly Phe Trp Pro Phe Gly Ser Phe Cys
                85                  90                  95

Asn Ile Trp Val Ala Phe Asp Ile Met Cys Ser Thr Ala Ser Ile Leu
            100                 105                 110

Asn Leu Cys Val Ile Ser Val Asp Arg Tyr Trp Ala Ile Ser Ser Pro
        115                 120                 125

Phe Arg Tyr Glu Arg Lys Met Thr Pro Lys Ala Ala Phe Ile Leu Ile
    130                 135                 140

Ser Val Ala Trp Thr Leu Ser Val Leu Ile Ser Phe Ile Pro Val Gln
145                 150                 155                 160

Leu Ser Trp His Lys Ala Lys Pro Thr Ser Pro Ser Asp Gly Asn Ala
                165                 170                 175

Thr Ser Leu Ala Glu Thr Ile Asp Asn Cys Asp Ser Ser Leu Ser Arg
            180                 185                 190

Thr Tyr Ala Ile Ser Ser Ser Val Ile Ser Phe Tyr Ile Pro Val Ala
        195                 200                 205

Ile Met Ile Val Thr Tyr Thr Arg Ile Tyr Arg Ile Ala Gln Lys Gln
    210                 215                 220

Ile Arg Arg Ile Ala Ala Leu Glu Arg Ala Ala Val His Ala Lys Asn
225                 230                 235                 240

Cys Gln Thr Thr Thr Gly Asn Gly Lys Pro Val Glu Cys Ser Gln Pro
                245                 250                 255

Glu Ser Ser Phe Lys Met Ser Phe Lys Arg Glu Thr Lys Val Leu Lys
            260                 265                 270

Thr Leu Ser Val Ile Met Gly Val Phe Val Cys Cys Trp Leu Pro Phe
        275                 280                 285

Phe Ile Leu Asn Cys Ile Leu Pro Phe Cys Gly Ser Gly Glu Thr Gln
    290                 295                 300

Pro Phe Cys Ile Asp Ser Asn Thr Phe Asp Val Phe Val Trp Phe Gly
305                 310                 315                 320

Trp Ala Asn Ser Ser Leu Asn Pro Ile Ile Tyr Ala Phe Asn Ala Asp
                325                 330                 335

Phe Arg Lys Ala Phe Ser Thr Leu Leu Gly Cys Tyr Arg Leu Cys Pro
            340                 345                 350

Ala Thr Asn Asn Ala Ile Glu Thr Val Ser Ile Asn Asn Asn Gly Ala
        355                 360                 365

Ala Met Phe Ser Ser His His Glu Pro Arg Gly Ser Ile Ser Lys Glu
    370                 375                 380
```

```
Cys Asn Leu Val Tyr Leu Ile Pro His Ala Val Gly Ser Ser Glu Asp
385                 390                 395                 400

Leu Lys Lys Glu Glu Ala Ala Gly Ile Ala Arg Pro Leu Glu Lys Leu
            405                 410                 415

Ser Pro Ala Leu Ser Val Ile Leu Asp Tyr Asp Thr Asp Val Ser Leu
            420                 425                 430

Glu Lys Ile Gln Pro Ile Thr Gln Asn Gly Gln His Pro Thr
            435                 440                 445
```

<210> SEQ ID NO 2
<211> LENGTH: 252
<212> TYPE: PRT
<213> ORGANISM: Artificial Sequence
<220> FEATURE:
<223> OTHER INFORMATION: The amino acid sequence of the modified red
      fluorescent protein

<400> SEQUENCE: 2

```
Leu Ser Ser Glu Arg Val Ser Glu Arg Met Tyr Pro Glu Asp Gly Ala
1               5                   10                  15

Leu Lys Ser Glu Ile Lys Lys Gly Leu Arg Leu Lys Asp Gly Gly His
            20                  25                  30

Tyr Ala Ala Glu Val Lys Thr Thr Tyr Lys Ala Lys Lys Pro Val Gln
            35                  40                  45

Leu Pro Gly Ala Tyr Ile Val Asp Ile Lys Leu Asp Ile Val Ser His
50                  55                  60

Asn Glu Asp Tyr Thr Ile Val Glu Gln Cys Glu Arg Ala Glu Gly Arg
65                  70                  75                  80

His Ser Thr Gly Gly Met Asp Glu Leu Tyr Lys Gly Thr Gly Gly Gly
                85                  90                  95

Ser Leu Val Ser Lys Gly Glu Glu Asp Asn Met Ala Ile Ile Lys Glu
            100                 105                 110

Phe Met Arg Phe Lys Val His Met Glu Gly Ser Val Asn Gly His Glu
            115                 120                 125

Phe Glu Ile Glu Gly Glu Gly Glu Gly Arg Pro Tyr Glu Ala Phe Gln
            130                 135                 140

Thr Ala Lys Leu Lys Val Thr Lys Gly Gly Pro Leu Pro Phe Ala Trp
145                 150                 155                 160

Asp Ile Leu Ser Pro Gln Phe Met Tyr Gly Ser Lys Ala Tyr Ile Lys
                165                 170                 175

His Pro Ala Asp Ile Pro Asp Tyr Phe Lys Leu Ser Phe Pro Glu Gly
            180                 185                 190

Phe Arg Trp Glu Arg Val Met Asn Phe Glu Asp Gly Gly Ile Ile His
            195                 200                 205

Val Asn Gln Asp Ser Ser Leu Gln Asp Gly Val Phe Ile Tyr Lys Val
            210                 215                 220

Lys Leu Arg Gly Thr Asn Phe Pro Pro Asp Gly Pro Val Met Gln Lys
225                 230                 235                 240

Lys Thr Met Gly Trp Glu Ala Tyr Asp Asp Leu
                245                 250
```

<210> SEQ ID NO 3
<211> LENGTH: 25
<212> TYPE: PRT
<213> ORGANISM: Artificial Sequence
<220> FEATURE:
<223> OTHER INFORMATION: The amino acid sequence of the signal peptide

```
<400> SEQUENCE: 3

Met Lys Thr Ile Ile Ala Leu Ser Tyr Ile Phe Cys Leu Val Phe Ala
1               5                   10                  15

Asp Tyr Lys Asp Asp Asp Ala Ser
            20              25

<210> SEQ ID NO 4
<211> LENGTH: 685
<212> TYPE: PRT
<213> ORGANISM: Artificial Sequence
<220> FEATURE:
<223> OTHER INFORMATION: Recombinant amino acid sequence comprising the
      amino acid sequence of dopamine receptor D1 type, the amino acid
      sequence of the modified red fluorescent protein, and the amino
      acid sequence of the signal peptide

<400> SEQUENCE: 4

Met Lys Thr Ile Ile Ala Leu Ser Tyr Ile Phe Cys Leu Val Phe Ala
1               5                   10                  15

Asp Tyr Lys Asp Asp Asp Ala Ser Ile Asp Met Arg Thr Leu Asn
            20                  25                  30

Thr Ser Ala Met Asp Gly Thr Gly Leu Val Val Glu Arg Asp Phe Ser
            35                  40                  45

Val Arg Ile Leu Thr Ala Cys Phe Leu Ser Leu Leu Ile Leu Ser Thr
    50                  55                  60

Leu Leu Gly Asn Thr Leu Val Cys Ala Ala Val Ile Arg Phe Arg His
65                  70                  75                  80

Leu Arg Ser Lys Val Thr Asn Phe Phe Val Ile Ser Leu Ala Val Ser
                85                  90                  95

Asp Leu Leu Val Ala Val Leu Val Met Pro Trp Lys Ala Val Ala Glu
            100                 105                 110

Ile Ala Gly Phe Trp Pro Phe Gly Ser Phe Cys Asn Ile Trp Val Ala
            115                 120                 125

Phe Asp Ile Met Cys Ser Thr Ala Ser Ile Leu Asn Leu Cys Val Ile
    130                 135                 140

Ser Val Asp Arg Tyr Trp Ala Ile Ser Ser Pro Ala Arg Tyr Glu Arg
145                 150                 155                 160

Lys Met Thr Pro Lys Ala Ala Phe Ile Leu Ile Ser Val Ala Trp Thr
                165                 170                 175

Leu Ser Val Leu Ile Ser Phe Ile Pro Val Gln Leu Ser Trp His Lys
            180                 185                 190

Ala Lys Pro Thr Ser Pro Ser Asp Gly Asn Ala Thr Ser Leu Ala Glu
            195                 200                 205

Thr Ile Asp Asn Cys Asp Ser Ser Leu Ser Arg Thr Tyr Ala Ile Ser
    210                 215                 220

Ser Ser Val Ile Ser Phe Tyr Ile Pro Val Ala Ile Met Ile Val Thr
225                 230                 235                 240

Tyr Thr Arg Ile Tyr Arg Ile Ala Gln Lys Gln Leu Ser Ser Glu Arg
                245                 250                 255

Val Ser Glu Arg Met Tyr Pro Glu Asp Gly Ala Leu Lys Ser Glu Ile
            260                 265                 270

Lys Lys Gly Leu Arg Leu Lys Asp Gly His Tyr Ala Ala Glu Val
            275                 280                 285

Lys Thr Thr Tyr Lys Ala Lys Lys Pro Val Gln Leu Pro Gly Ala Tyr
    290                 295                 300

Ile Val Asp Ile Lys Leu Asp Ile Val Ser His Asn Glu Asp Tyr Thr
```

```
            305                 310                 315                 320
Ile Val Glu Gln Cys Glu Arg Ala Gly Arg His Ser Thr Gly Gly
                325                 330                 335

Met Asp Glu Leu Tyr Lys Gly Gly Thr Gly Gly Ser Leu Val Ser Lys
                340                 345                 350

Gly Glu Glu Asp Asn Met Ala Ile Ile Lys Glu Phe Met Arg Phe Lys
                355                 360                 365

Val His Met Glu Gly Ser Val Asn Gly His Glu Phe Glu Ile Glu Gly
            370                 375                 380

Glu Gly Glu Gly Arg Pro Tyr Glu Ala Phe Gln Thr Ala Lys Leu Lys
385                 390                 395                 400

Val Thr Lys Gly Gly Pro Leu Pro Phe Ala Trp Asp Ile Leu Ser Pro
                405                 410                 415

Gln Phe Met Tyr Gly Ser Lys Ala Tyr Ile Lys His Pro Ala Asp Ile
                420                 425                 430

Pro Asp Tyr Phe Lys Leu Ser Phe Pro Glu Gly Phe Arg Trp Glu Arg
                435                 440                 445

Val Met Asn Phe Glu Asp Gly Gly Ile Ile His Val Asn Gln Asp Ser
            450                 455                 460

Ser Leu Gln Asp Gly Val Phe Ile Tyr Lys Val Lys Leu Arg Gly Thr
465                 470                 475                 480

Asn Phe Pro Pro Asp Gly Pro Val Met Gln Lys Lys Thr Met Gly Trp
                485                 490                 495

Glu Ala Tyr Asp Asp Leu Lys Arg Glu Thr Lys Val Leu Lys Thr
                500                 505                 510

Leu Ser Val Ile Met Gly Val Phe Val Cys Cys Trp Leu Pro Phe Phe
            515                 520                 525

Ile Leu Asn Cys Ile Leu Pro Phe Cys Gly Ser Gly Glu Thr Gln Pro
                530                 535                 540

Phe Cys Ile Asp Ser Asn Thr Phe Asp Val Phe Val Trp Phe Gly Trp
545                 550                 555                 560

Ala Asn Ser Ser Leu Asn Pro Ile Ile Tyr Ala Phe Asn Ala Asp Phe
                565                 570                 575

Arg Lys Ala Phe Ser Thr Leu Leu Gly Cys Tyr Arg Leu Cys Pro Ala
                580                 585                 590

Thr Asn Asn Ala Ile Glu Thr Val Ser Ile Asn Asn Asn Gly Ala Ala
            595                 600                 605

Met Phe Ser Ser His His Glu Pro Arg Gly Ser Ile Ser Lys Glu Cys
                610                 615                 620

Asn Leu Val Tyr Leu Ile Pro His Ala Val Gly Ser Ser Glu Asp Leu
625                 630                 635                 640

Lys Lys Glu Glu Ala Ala Gly Ile Ala Arg Pro Leu Glu Lys Leu Ser
                645                 650                 655

Pro Ala Leu Ser Val Ile Leu Asp Tyr Asp Thr Asp Val Ser Leu Glu
                660                 665                 670

Lys Ile Gln Pro Ile Thr Gln Asn Gly Gln His Pro Thr
                675                 680                 685

<210> SEQ ID NO 5
<211> LENGTH: 1329
<212> TYPE: DNA
<213> ORGANISM: Artificial Sequence
<220> FEATURE:
<223> OTHER INFORMATION: cDNA sequence of dopamine receptor D1 type
```

<400> SEQUENCE: 5

```
atggaccctc tgaatctgtc atggtatgac gatgatctgg aaaggcaaaa ctggtcccgg      60
ccgtttaatg gatcagatgg taaagcagat cggcctcact acaattacta cgccacactg     120
ctcaccctcc tcattgcagt tattgtgttc gggaacgtgc tggtttgcat ggcagtaagc     180
cgggaaaagg ctctccagac aactaccaac tacctcatcg tctcacttgc ggtagcagac     240
ttgctggtgg ctaccctggt catgccttgg gtggtttact tggaggttgt tggcgagtgg     300
aagttctcaa ggatacattg cgatatcttt gtaaccctgg atgttatgat gtgtacggct     360
tcaatattga acctctgtgc catctccatc gaccgctata ctgccgtagc aatgcctatg     420
ctttacaata cccgatattc aagcaagcgg agggtgacgg ttatgatttc atcgtttgg      480
gtgctgtcct ttacgattag ttgccctctg ctgttcgggc tgaacaacgc agaccaaaat     540
gagtgtatta ttgccaatcc cgcctttgtg gtgtattcat caattgtgag cttttacgtc     600
ccatttattg ttacattgtt ggtgtacatt aaaatataca ttgtcctcag gcggcggaga     660
aaacgggtga acaccaagcg gtcatctaga gctttccgcg ctcatctgag agctccactg     720
aagggcaact gtacccaccc ggaagacatg aaactgtgta ccgtcatcat gaaatccaat     780
gggagcttcc ccgttaatag gcggagagtg gaagccgcaa ggcgcgcaca ggagctggag     840
atggagatgc tcagcagcac cagcccccct gagcgcaccc ggtacagccc cattccgccc     900
tcacatcacc aactcacact gcccgacccc tcacatcatg gactccactc taccccggac     960
tcaccggcca agcctgaaaa gaacgggcac gcgaaagatc acccgaaaat cgctaagatt    1020
ttcgagatcc aaactatgcc taacggcaaa actcgcacct ctctgaaaac aatgagtcgg    1080
agaaaacttt cacagcaaaa ggagaagaag gccacccaaa tgctggccat tgtactcggg    1140
gtgttcatca tttgttggct gcccttttt atcacccaca tcctgaacat tcattgtgat    1200
tgcaacattc caccagtgct ctatagcgcc tttacttggc tgggttatgt gaatagtgcg    1260
gtaaacccca taatctacac cacattcaat atcgaatttc gaaaagcatt tctgaagatt    1320
ctccactgt                                                           1329
```

<210> SEQ ID NO 6
<211> LENGTH: 756
<212> TYPE: DNA
<213> ORGANISM: Artificial Sequence
<220> FEATURE:
<223> OTHER INFORMATION: cDNA sequence of cpRFP

<400> SEQUENCE: 6

```
ctgagctcac ccgtggtttc cgagcggatg taccccgagg acggcgccct gaagagcgag      60
atcaagaagg ggctgaggct gaaggacggc ggccactacg ccgccgaggt caagaccacc     120
tacaaggcca agaagcccgt gcagctgccc ggcgcctaca tcgtggacat caagttggac     180
atcgtgtccc acaacgagga ctacaccatc gtggaacagt gcgaacgcgc cgagggccgc     240
cactccaccg gcggcatgga cgagctgtac aaggaggta caggcgggag tctggtgagc     300
aagggcgagg aggataacat ggccatcatc aaggagttca tgcgcttcaa ggtgcacatg     360
gagggctccg tgaacggcca cgagttcgag atcgagggcg agggcgaggg ccgcccctac     420
gaggcctttc agaccgctaa gctgaaggtg accaagggtg gccccctgcc cttcgcctgg     480
gacatcctgt cccctcagtt catgtacggc tccaaggcct acattaagca cccagccgac     540
atccccgact acttcaagct gtccttcccc gagggcttca ggtgggagcg cgtgatgaac     600
ttcgaggacg gcggcattat tcacgtgaac caggactcct ccctgcagga cggcgtattc     660
```

```
atctacaagg tgaagctgcg cggcaccaac ttcccccccg acggccccgt aatgcagaag    720
aagaccatgg gctgggaggc tacgcgtgac gacctg                              756
```